ARALIA PLANT
Filed April 8, 1974
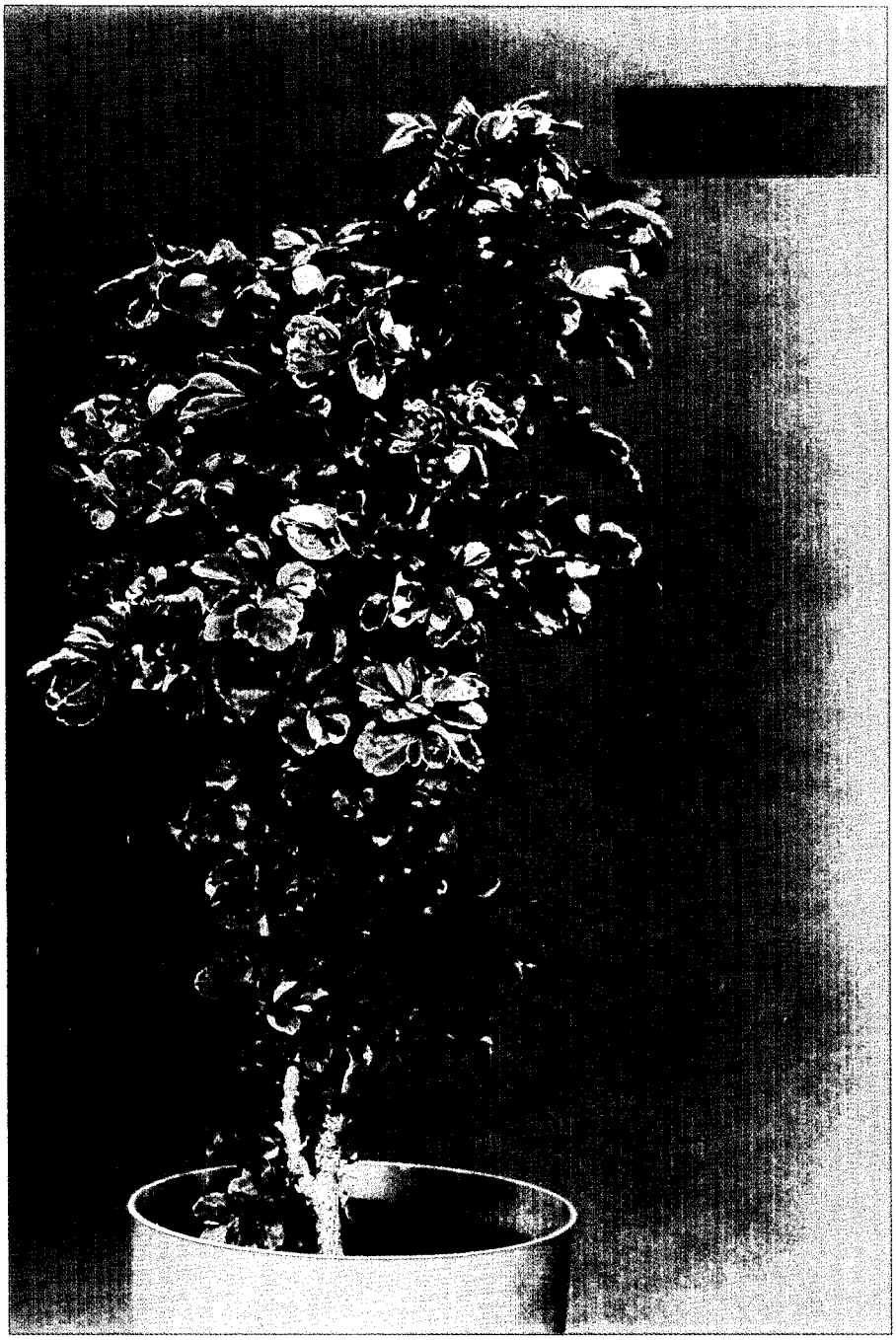

United States Patent

Plant Pat. 3,775
Patented Aug. 26, 1975

3,775

ARALIA PLANT

Joseph W. Hoak, 17040 SW. 90th Ave., Miami, Fla. 33157

Filed Apr. 8, 1974, Ser. No. 459,110
Int. Cl. A01h *5/00*
U.S. Cl. Plt.—88 1 Claim

This invention relates to a new and distinct variety of Aralia plant and is a result of a sport in the production of *Polyscias* (*Aralia*) *balfouriana minifolia* in Hoak's Nursery in Miami, Fla. The origin of the descriptive word "*minifolia*" in the recognized variety *Polyscias balfouriana* is unknown to the applicant, other than to say that it has been in general use by nurserymen in the South Florida area to describe an Aralia plant having smaller leaves than those of the *balfouriana* variety. I have named my new variety "Aralia Palapala." This new variety has been asexually reproduced and propagated by cuttings for a period of over five years since the first mutation was discovered, with no reversal to the original variety, *Polyscias balfouriana minifolia*. This sport came about as a variant of a green *Polyscias balfouriana minifolia* that was growing in a shade house on the south end of Hoak's greenhouse and nursery in Miami, Fla. When transplanted to the outside at the back of the greenhouse it was cut back. One year later one branch came back as a sport. After propagating this sport for about 5 years, cuttings were placed in a back slat house in cutting boxes. When of potting size, these were transplanted to 10 inch pots and moved to Hoak's Silver Palm Nursery, Goulds, Fla. where they are at this time.

My new variety differs from the parent *Polyscias* (*Aralia*) *balfouriana minifolia* in that the leaves, instead of being substantially forest green in coloration as in the industry standard, display distinctive partial yellowish coloration. The color characteristics of my new variety, according to Exotica Horticultural Color Guide, A.B. Graph Exotica III, Roehrs Co., publisher, 1970 edition, page 37 are as shown in the following table:

| | *Plate* | *Letter* | *No.* |
|---|---|---|---|
| Yellowish portions of leaf | 1 | P | 1 |
| Green portions of leaf | 77 | B | 7 |
| Back of leaf | 76 | D | 6 |
| Petiole | 42 | B | 7 |
| Stem | 8 | P | 1 |

The distinctive yellowish coloration at marginal edge portions of the leaves extends inwardly to various irregular patches of such average size that in the mature plant most of the leaves will display from about 25 to 50% of yellowish coloration. My new plant carries from 3 to 5 leaves on each stem, which leaves measure about 1½ inches both in length and in width, on the average. An important feature of my new variety resides in the irregularity of the marginal edges of the leaves as distinguished from the comparatively smooth-edged leaves of its parent, *Polyscias balfouriana minifolia.*

My new variety thrives as an ornamental shrub or bush and its distinctive leaf coloration and formation make it a most attractive plant. As noted above, the particular distinguishing characteristics of my new variety as compared with the industry standard *Aralia balfouriana minifolia* reside firstly, in the variegated yellow coloration of the leaves, and secondly, the distinctive irregular marginal edges of the leaves.

Having thus described my invention I claim:

1. A new distinct variety of *Polyscias balfouriana minifolia* substantially as herein shown and described, characterized particularly as to novelty by having basically forest green leaves displaying light to dark yellow coloration beginning at marginal outer edge portions thereof and extending inwardly in irregularly formed patches constituting between approximately 25 to 50% of leaf area, and further being distinguished by having distinctive irregular marginal edges of the leaves as compared with the relatively smooth edges of the parent plant.

References Cited

Exotica III, Graph, 1963, Roehrs Co., Rutherford, N.J., pp. 251 and 1696 relied on.

ROBERT E. BAGWILL, Primary Examiner